United States Patent [19]
Law et al.

[11] Patent Number: 5,938,690
[45] Date of Patent: *Aug. 17, 1999

[54] PAIN MANAGEMENT SYSTEM AND METHOD

[75] Inventors: Jay Law, Denver, Colo.; William Borkan, North Miami Beach, Fla.; Lance Ehren, Dallas, Tex.; George Van Campen, Fort Lauderdale, Fla.

[73] Assignee: Advanced Neuromodulation Systems, Inc., Allen, Tex.

[*] Notice: This patent issued on a continued prosecution application filed under 37 CFR 1.53(d), and is subject to the twenty year patent term provisions of 35 U.S.C. 154(a)(2).

[21] Appl. No.: 08/659,874

[22] Filed: Jun. 7, 1996

[51] Int. Cl.$^6$ ........................................................ A61N 1/02
[52] U.S. Cl. .............................................. 607/46; 607/63
[58] Field of Search .............................. 607/1, 2, 43, 46, 607/117, 52, 62–64; 128/741; 600/554

[56] References Cited

U.S. PATENT DOCUMENTS

| | | |
|---|---|---|
| 3,888,261 | 6/1975 | Maurer . |
| 3,920,025 | 11/1975 | Stasz et al. . |
| 4,026,301 | 5/1977 | Friedman et al. .................. 607/43 |
| 4,167,190 | 9/1979 | Sorenson et al. . |
| 4,230,121 | 10/1980 | Stanton . |
| 4,379,462 | 4/1983 | Borkan et al. . |
| 4,390,023 | 6/1983 | Rise . |
| 4,398,537 | 8/1983 | Holmbo . |
| 4,459,989 | 7/1984 | Borkan . |
| 4,612,934 | 9/1986 | Borkan . |
| 4,690,144 | 9/1987 | Rise et al. . |
| 4,744,371 | 5/1988 | Harris . |
| 4,793,353 | 12/1988 | Borkan . |
| 5,031,618 | 7/1991 | Mullett . |
| 5,058,584 | 10/1991 | Bourgeois . |
| 5,119,832 | 6/1992 | Xavier . |
| 5,121,754 | 6/1992 | Mullett . |
| 5,207,218 | 5/1993 | Carpentier et al. . |
| 5,251,634 | 10/1993 | Weinberg . |

(List continued on next page.)

OTHER PUBLICATIONS

"Spinal Cord Stimulation for Chronic, Intractable Pain: Experience Over Two Decades" Neurosurgery, vol. 32, No. 3, Mar., 1993.

"Spinal Cord Stimulation for Chronic Pain" Neurosurgery Clinics of North America, vol. 6, No. 1, Jan. 1995.

"Spinal Cord Stimulation for Chronic, Intractable Pain: Superiority of "Multi–Channel" Devices" Pain, 44(1991), 119–130.

"The Role of Spinal Cord Stimulation in Contemporary of Pain Management", APS Journal 2(2): 91–99, 1993.

"Patient–Interactive, Computer–Controlled Neurological Stimulation System: Clinical Efficacy in Spinal Cord Stimulator Adjustment", Neurosurg., vol. 76, Jun. 1992.

(List continued on next page.)

Primary Examiner—William E. Kamm
Assistant Examiner—George R. Evanisko
Attorney, Agent, or Firm—Sidley & Austin

[57] ABSTRACT

A computer based system and methods for use with known neuromodulation systems to assist in the performance of pre-, intra- and post-operative procedures relating to the determination and optimization of a patient's therapeutic regimen. The system can use a computer database of information in connection with the pain map of an individual patient to aid the physician in making more accurate decisions regarding waveform and electrode configuration definition, as well as multi-electrode lead placement. The system can record and process patient responses to test stimulation patterns during the operation of placing the electrodes, so as to give the physician real-time information that can be used to effectively position the multi-electrode leads within the patient's body. The system also provides computer assisted post-operative presentation and assessment of stimulation settings, which utilizes, at least in one mode of operation, an iterative, systematic approach to determining one or more optimum stimulation settings.

26 Claims, 5 Drawing Sheets

U.S. PATENT DOCUMENTS

| | | |
|---|---|---|
| 5,342,409 | 8/1994 | Mullett ....................................... 607/46 |
| 5,370,672 | 12/1994 | Fowler et al. . |
| 5,374,285 | 12/1994 | Vaiani et al. . |
| 5,417,719 | 5/1995 | Hull et al. . |
| 5,423,877 | 6/1995 | Mackey . |
| 5,425,364 | 6/1995 | Imran . |
| 5,443,486 | 8/1995 | Hrdlicka et al. . |
| 5,458,631 | 10/1995 | Xavier . |
| 5,462,545 | 10/1995 | Wang et al. . |
| 5,653,739 | 8/1997 | Maurer et al. ............................ 607/46 |

OTHER PUBLICATIONS

"Spinal Cord Stimulation for Chronic, Intractable Pain", Richard B. North, Electrical and Magnetic Stimulation of the Brain and Spinal Cord, Copyright 1993, Chapter 25, pp. 289–301.

Computer–controlled Spinal Cord Stimulation Shown Superior to Conventional Programming, Anesthesiology News, Jun. 1996.

PAIN MANAGEMENT SYSTEM AND METHOD

BACKGROUND

The present invention relates to a neuromodulation system for managing pain and/or various motor disorders. More specifically, the invention relates to a specially programmed computer system for use with known neuromodulation systems to assist in the performance of pre-, intra- and post-operative procedures relating to the determination and optimization of a patient's therapeutic regimen.

A neuromodulation system can deliver stimulation to tissue or nerve centers for the treatment of nervous or muscular disorders. One class of neuromodulation systems includes spinal cord stimulation (SCS) systems, which deliver a particularized electrical pulse to a specified region of a patient's spinal cord to effect the management of chronic or acute pain.

An SCS system includes a pulse generator, whether of a totally implanted or an RF-coupled nature, which delivers an electrical pulse through at least one multi-electrode lead positioned within the epidural space of a patient. It is the intention to position the lead so that the delivered electrical energy is directed to particular spinal nerve roots and/or nerve bundles associated with one or more pain-afflicted dermatomes. The delivered electrical pulse, practically, creates an analgesic effect, masking the pain sensed by the patient.

As the use of electrical energy for pain management or the treatment of motor disorders is an inexact science, an optimum therapeutic regimen must be determined. For any neuromodulation system utilizing an electrical pulse, this requires defining a pulse waveform (e.g., signal pulse width, frequency, phase and amplitude), as well as determining the proper multi-electrode lead position and electrode polarity configuration. Current SCS devices allow each of these parameters, excluding lead position, to be modified non-invasively.

A typical RF-coupled SCS system will include an implanted receiver that receives pulse information from an external transmitter. The external transmitter can be programmed with waveforms and treatment (dose) times. As mentioned above, the electrodes are arrayed on lead(s) which are electrically coupled to the receiver. Each electrode is capable of assuming a positive, negative or neutral polarity. One such system is described in detail in U.S. Pat. No. 4,612,934, the disclosure of which is incorporated herein by reference.

Current SCS systems may use one or two multi-electrode leads, with each lead possessing between four and eight electrodes positioned along the distal end of the lead. As the number of available electrodes increase, the possible number of electrode combinations (a "combination" including at least one cathode and anode), increases disproportionately. Accordingly, computer assistance in programming and assessing these electrode combinations and waveform variations would be beneficial. Specifically, computer programming and evaluation assistance would enable a reduction in the time needed by the patient and physician to optimize the therapeutic regimen.

The use of a computer interface to aid in selecting stimulation patterns is disclosed in U.S. Pat. No. 5,370,672. That system discloses a tablet and stylus input device used by the patient to draw a topographical sketch, relative to a human representation, of the pain being experienced. This sketch, or "pain map," is then compared for overlap with a sketch made of the patient's experienced or perceived area(s) of paresthesia ("paresthesia" meaning the perceived sensation produced by electrical stimulation of nerve roots and/or nerve bundles). The system of the '672 patent also allows the patient or physician to adjust the treatment regimen to attain better concordance between the areas of pain and areas of stimulation. Notwithstanding, the '672 patent does not include pre-operative or intra-operative features that can be instrumental to the success of achieving effective stimulation, whereas improper lead placement may prevent optimum or even adequate stimulation. Moreover, the '672 patent teaches the use of random presentation of electrode configurations to determine an optimum configuration. Although such method may avoid sampling bias, this unstructured and unfocused approach inherently requires the sampling of a large population to ensure that worthy data (i.e., that which is capable of leading to positive or effective stimulation) is obtained.

One object of this invention is to use a computer database of information in connection with the pain map of an individual patient to aid the physician in making more accurate decisions regarding waveform and electrode configuration definition as well as multi-electrode lead placement.

In addition, it would be very useful to have the ability to record and process patient responses to test stimulation patterns during the operation of placing the electrodes, so as to give the physician real-time information that can be used to effectively position the multi-electrode leads within the patient's body. Thus, another object of this invention is to use computing power to process patient responses to test stimulation patterns that are applied during the implantation procedure and provide the physician with information that can be used to make decisions regarding lead placement and stimulation settings.

Finally, another object of the present invention is to provide computer assisted post-operative presentation and assessment of stimulation settings, which utilizes, at least in one mode of operation, an iterative, systematic approach to determining one or more optimum stimulation settings.

SUMMARY OF THE INVENTION

The basic components of the present invention are a personal pen computer, a neuromodulation system, and software. Although "neuromodulation system" may include any number of devices for the treatment of pain or other disorders, to which the present invention will have equal application, this disclosure will use an RF-coupled spinal cord stimulation (SCS) system for the purposes of illustration. The software presents inquiries to the patient/physician, records patient/physician responses, stores data, reads information stored in the transmitter, transfers new or modified programming information to the transmitter for localized storage, permits control of the transmitter, and performs calculations resulting in displayed information or suggestions that can be used by the physician/patient to facilitate improved treatments. In short, through use of a specially programmed general purpose computer that communicates with the electronics of a neuromodulation system, the present system and method provides an informational database, a method for recording pain, and a standardized method of creating and recording pain treatments interactively. The system will assist doctors and patients by receiving and storing the procedures and treatment data to the computer database. The system will also allow the patient to assist in the optimization of performance by leading the patient through a series of suggested combinations to try (each combination may be accepted or rejected) and recording the stimulation effects for the physician's later evaluation.

Pre-operatively, a patient enters a pain topography which represents the patient's experienced pain. Further, the patient may be presented with and asked to respond to various questions relating to insurance coverage, medical history, psychological history and the like. The computer can present the physician with a graphical representation of the associated dermatomes and the spinal origin of the nerve bundles affected by the patient-described pain. The system correlates the pre-operative data and can offer alternative treatment possibilities to consider for each patient. From such possibilities, the physician can evaluate any number of possible electrode configurations as well as evaluate the suggested spinal levels for electrode placement.

During implantation of the electrodes, the system assimilates the patient's various responses to test stimulation settings. For certain types of pain, where delivery of an electric pulse to the spine's physiological "midline" is critical, the present invention provides a means of assessing the location and region of influence of the electrical stimulation. The computer can further record the degree of physiological symmetry and region of stimulation influence of the delivered electrical pulse(s) for each such test stimulation pattern. From a patient-entered stimulation topography, the computer can calculate the amount of overlap between the previously entered pain topography and the patient's perceived stimulation. From this and other information provided by the system, the physician can better decide whether to reposition the implanted lead(s), implant additional leads, modify the programmed waveform and/or electrode combination, or select another waveform and/or electrode combination altogether.

Post-operatively, the system provides a variety of means to optimize, program and assess waveform and electrode combinations. In particular, the system provides at least one mode in which a basic electrode configuration is used to iteratively and systematically administer and assess a number of stimulation settings (i.e., waveforms and electrode combinations). The effect of such assessment is the determination and potential use of one or more discovered stimulation settings which most effectively address the patient's unique pain topography.

All of the above methods can be accomplished using a properly programmed pen or laptop computer linked via a common serial port to a transmitter of a neuromodulation system. Preferably a graphical interface, such as Pen Windows, is used so that much of the data presentation, recording of responses, and adjustment of waveform and electrode configuration parameters can be accomplished with pen or mouse inputs to screens that guide the patient or physician through the necessary steps of entering patient-specific information.

DETAILED DESCRIPTION

In order to illustrate the preferred embodiment of the system and method, the following is a detailed description of the options presented by the system to the user, the patient/physician interactions with the system, and the methods for determining improved treatment regimens facilitated by using the system. These descriptions are set forth for each of the main modes of operation of the system, namely, pre-operative, intra-operative, and post-operative.

Figure 1:
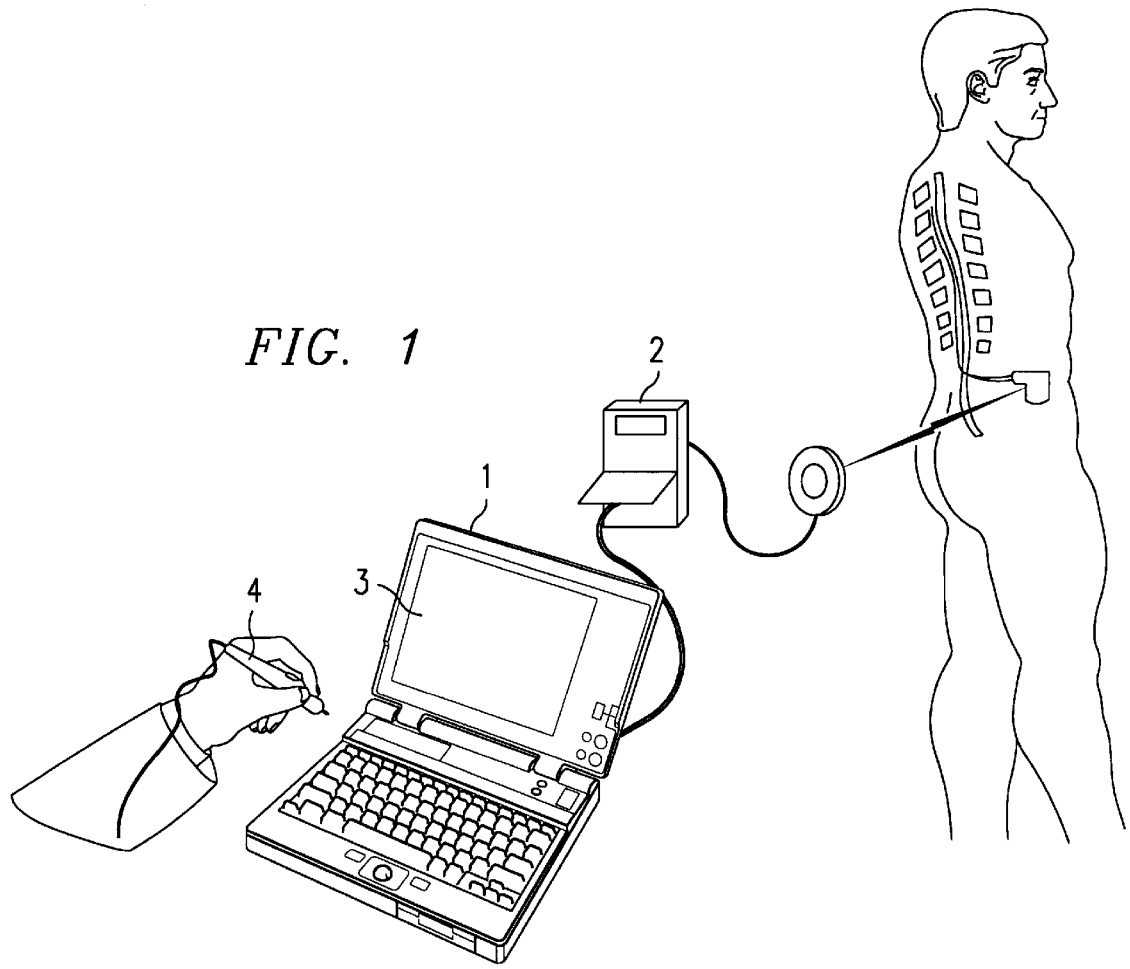
FIG. 1, is a schematic view of the system, including a general purpose computer connected to a transmitter and the outline of a patients body in which a receiver and electrode leads have been implanted.

Referring to FIG. 1, the main components of the system are a general purpose computer 1, a neuromodulation transmitter 2, and software. The computer 1 should preferably have the ability to receive inputs via the screen 3 through use of a stylus 4 or mouse (not shown). The preferred system of the invention uses a laptop computer 1 equipped with a stylus 4 and Pen Windows ™ operating system. Some means for transferring data from the computer 1 to the transmitter 2 must also be provided. In the preferred embodiment, the computer 1 and transmitter 2 include an industry standard serial communication port which may be electrically coupled by a standard ribbon cable. Infra-red, radio-frequency and ultrasonic sound transmission between the computer 1 and transmitter 2, to provide more freedom of movement to the user, are also options. The software resides in the storage memory of the computer 1.

When the system is started, a screen is displayed into which patient information can be entered or existing patient information can be retrieved for review. After a patient has been selected (or new patient information has been entered), a screen appears that allows the user to select one of the procedure types from the choices of: pre-operative (procedures and functions useful to the physician in the pre-operative stage of treatment to aid in evaluating the patient physical and mental condition, selecting a particular neuromodulation system and determining a spinal level for electrode placement; intra-operative (procedures and functions useful to the physician during the implantation and positioning of the multi-electrode lead(s) arrays and implanted portion of the neuromodulation system); and post-operative (procedures and functions useful in optimizing the stimulation settings of previously implanted and programmed neuromodulation systems).

Pre-Operative Procedures Group

Figure 2:
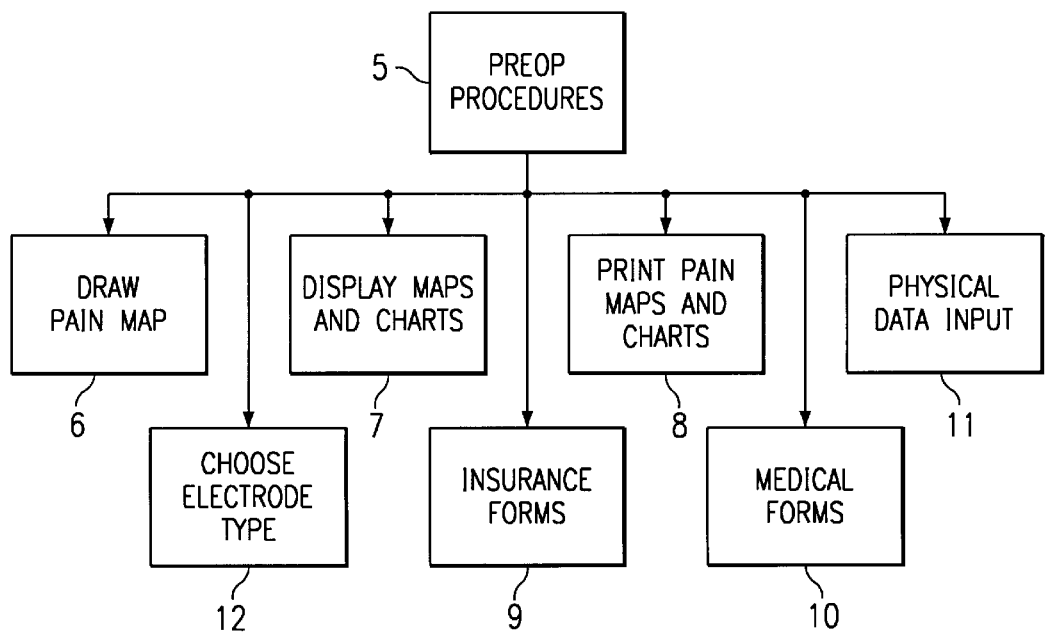
FIG. 2, is a flow diagram showing the pre-operation procedures that can be performed using the system of the invention.

In the preferred embodiment of the present invention, upon entering the pre-operation procedures group, the screen (or other display device) provides a number of options for the user, each such option relating to either the pre-operative provision of data regarding the patient's experienced pain or the patient's biographical information and medical history. In regard to defining the patient's pain, referring to FIG. 2, the user may select the Draw Pain Map mode 6. In this mode, the computer can receive and store graphical data coinciding with areas of a patient's body which experience pain. This is known in the art as "pain mapping."

The Draw Pain Map mode 6 is used to allow the patient to draw the patient's pain information, relative to a human depiction provided on the computer screen or other display device. One method of entering such data includes requesting the patient to draw two pain topographies, or maps, one addressing the patient's overall pain and another concerning the patient's most intense pain ("worst pain map"). For both pain map entry screens, the computer presents a human depiction having both a front and rear view. The patient simply indicates the experienced pain by placing the stylus 4 within proximity of the desired regions of the human depiction (provided that this is the hardware configuration being used). The preferred embodiment of the computer software will only allow areas within the body outline of the human depiction to be shaded. The software further includes editing capabilities which allows once-entered information to be removed or modified. For distinguishing the indicated regions of pain, the user is prompted to qualify the magnitude of the perceived pain (based upon a relative scale, for example, 0–10) for each map. This information, like all information requested by the computer system 1, is preferably entered through on-screen controls or keyboard entries.

If a user edits an existing pain map, the computer software will store the most current revisions without overwriting the older map. Accordingly, the computer system 1 will utilize the information from such revisions for all subsequent displays, computations and procedures. In the preferred embodiment, upon completing the entry of the patient's pain data, the user can review certain information through the Display Maps and Charts screen 7, such information deriving from the patient's most current pain information. The preferred embodiment includes the option to view a dermatome chart, a segmented dermatome chart, a spinal representation, or a summary pain map (superimposing the patient's worst pain data upon the patient's overall pain data).

Figure 5:
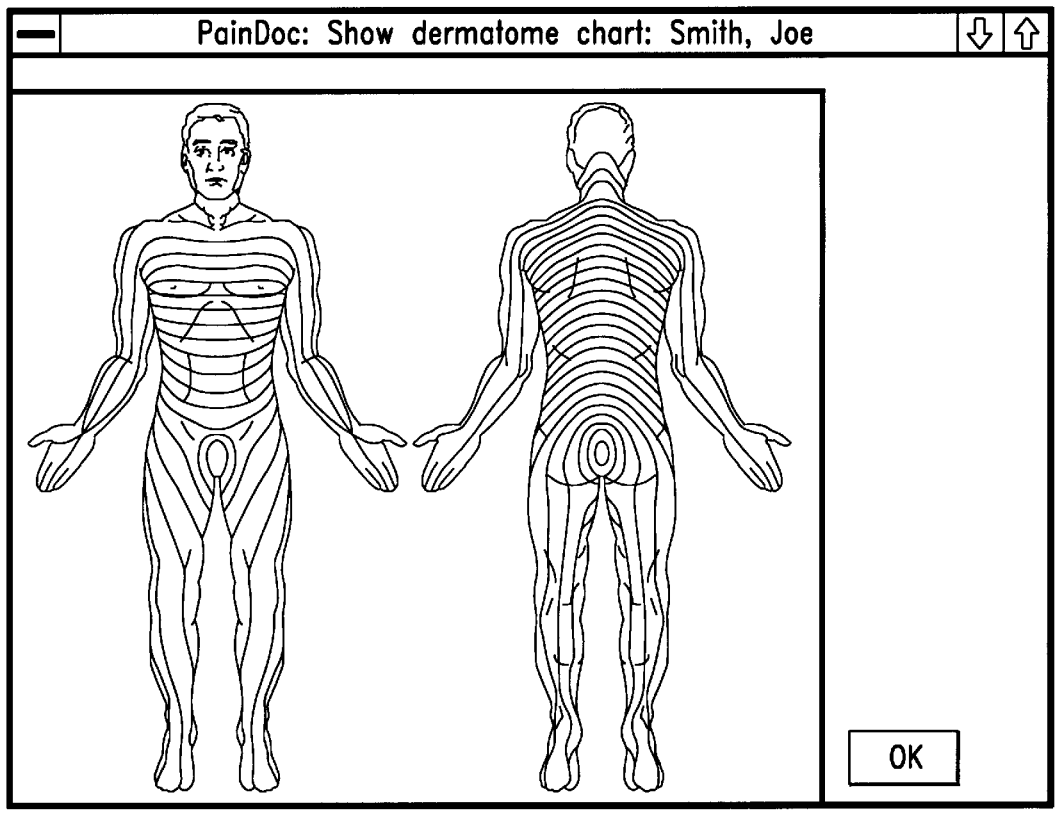
FIG. 5 is a depiction of the dermatome display of the system, showing a graphical representation of the standardized dermatomes of the human body.

Referring to FIG. 5, the dermatome and segmented dermatome charts show the correspondence between the reported areas of the patient's pain and the dermatomes of the human body. In preparing either of the dermatome charts, the computer software compares the pain map drawn by the patient to a database-stored, standardized graphical representation of a human dermatome map. Specifically, the computer system 1 graphically compares the pixels representing the patient's pain to the pixels of the underlying dermatomes. As may be understood, each dermatome can be assigned some percentage of pain overlay (i.e., ranging from 0 to 100%). Using a threshold percentage (for example, 30%), the computer system 1 will denote those dermatomes whose overlay percentage meets or exceeds this threshold percentage.

The segmented dermatome chart differs from the other dermatome chart only in the regard that each dermatome is subdivided. The predefined subdivision provides the physician more specific understanding of the affected regions. Functionally, the preparation of the segmented dermatome chart does not differ from that described above, excepting that each dermatome segment undergoes an independent overlay percentage determination.

Figure 6:
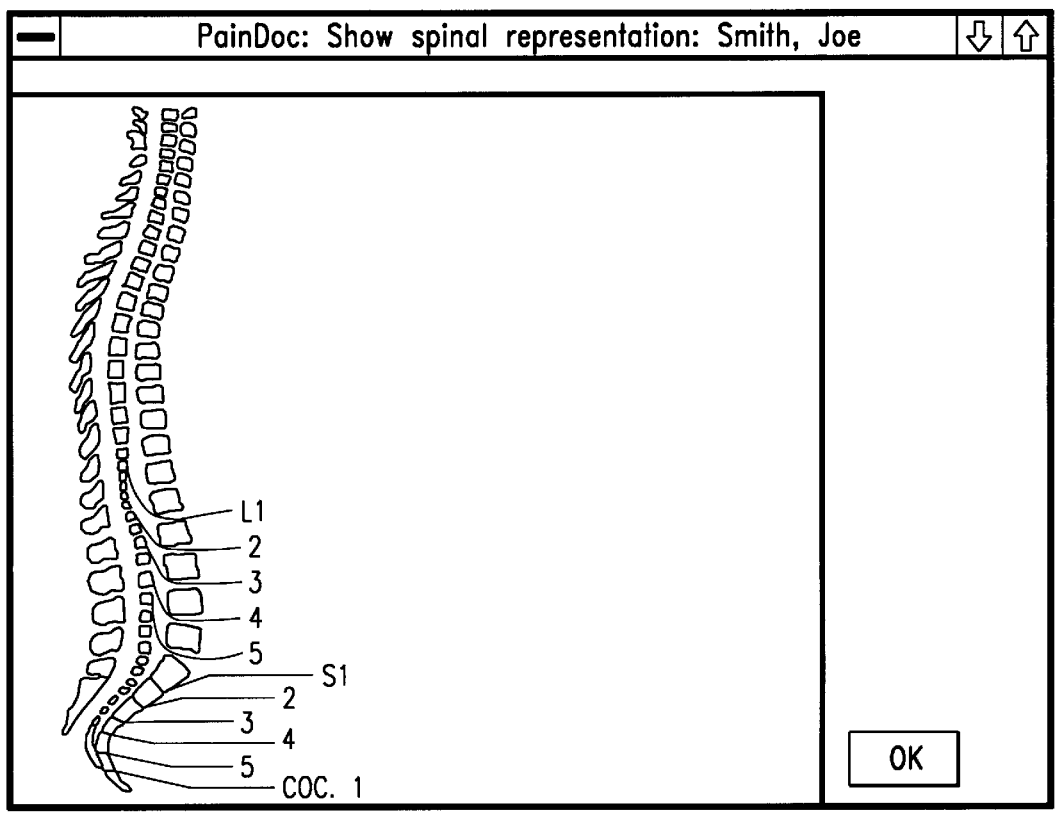
FIG. 6 is a depiction of the spinal display of the system, showing spinal levels that correspond to indicated segments of the dermatome map that are overlapped by areas of a pain map.

Referring to FIG. 6, the computer system 1 can further present the patient's pain information in the context of the affected nerve and/or nerve roots which join the spinal cord at a particular location along the vertebral column ("spinal level"). Consequently, this information as well as that provided by the dermatome charts may suggest to the physician the ideal location in which the multi-electrode lead(s) may be positioned to afford the greatest opportunity to address the patient's pain.

The present invention permits the user to print any of the above maps, including previous maps, and charts. Referring to FIG. 1, printing may be accomplished through Print Pain Maps and Charts screen 8 (a like function exists in the intra-operative and post-operative procedure groups, see FIGS. 3 and 4, respectively).

In addition to the above functionality, the pre-operation mode of the system can be used to store important information regarding the patient that will be available for use and review in any subsequent update or the treatment. As spinal cord stimulation for the purpose of pain management has empirically been shown to be more effective for patients having a specific psychological profile, physical condition and pain type, the system of the present invention provides a means of assessing and screening patients through the Medical Forms screen 10. Moreover, insurance information can be stored with the patient's record by using Insurance Forms screen 9. Physical Data Input screen 11 permits the entry of certain information that may be of importance during the subsequent implantation of a patient, such information may include the physical dimensions of the patient's epidural space, conus location as well as any other like information.

Choosing Electrode Type screen 12 provides a means for the physician to enter product information or descriptions of the patient's proposed neuromodulation system (e.g., number of leads, lead type, transmitter type) based on the above pre-operative assessment. Alternatively, in one embodiment of the present invention, screen 7 can also present the computer system's suggestion concerning proposed neuromodulation systems, such suggestion being the product of an evaluation of available neuromodulation systems, the patient's medical condition and the nature of the patient's pain.

Figure 3:
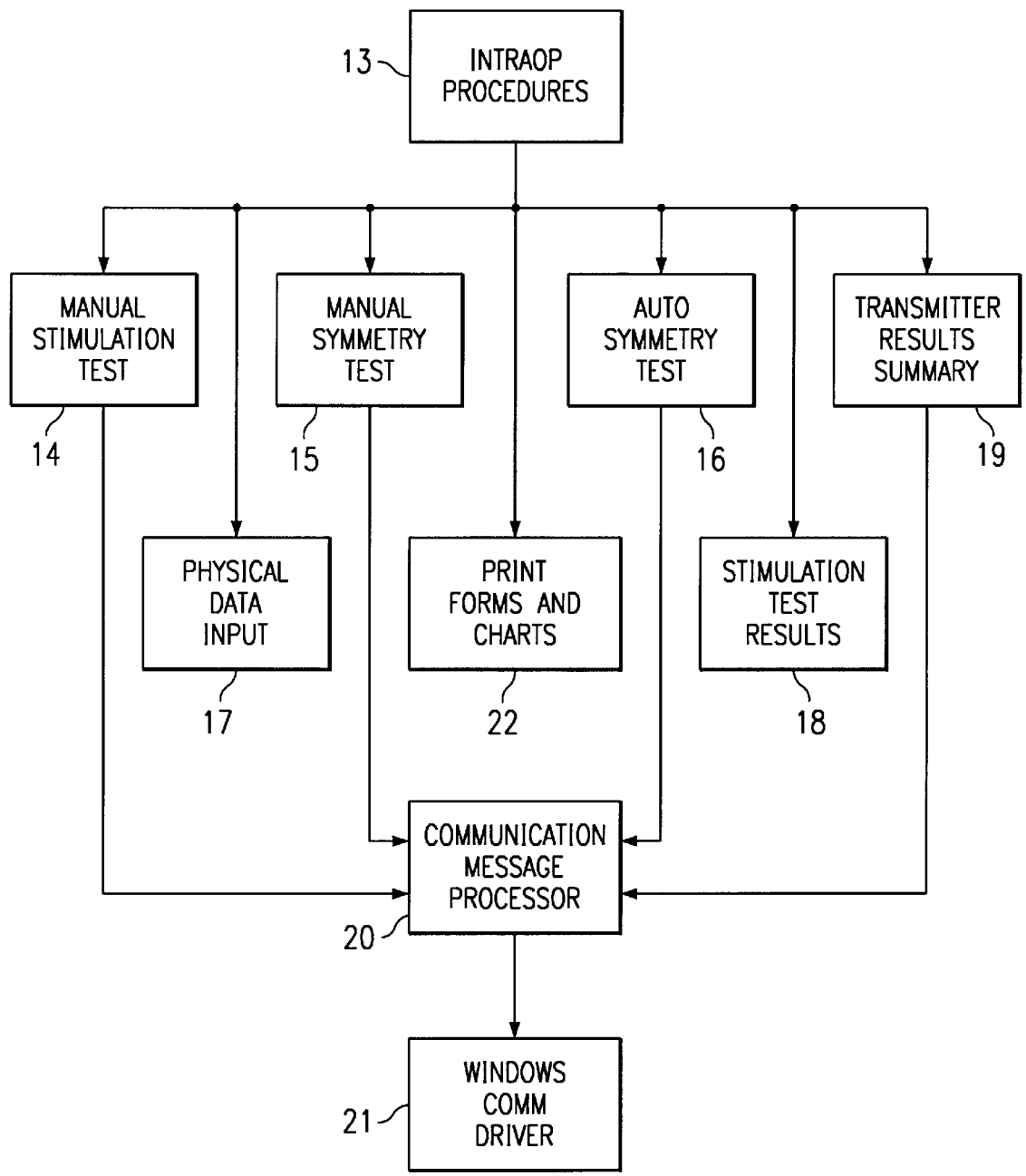
FIG. 3, is a flow diagram of the intra-operation procedures that can be performed using the system of the invention.

Intra-Operative Procedures Group The system of the present invention also operates to provide intra-operative verification of the electrode locations and stimulation effectiveness during the implantation procedure. Referring to FIG. 3, the intra-operative procedure group allows the user to select a manual stimulation test, a manual symmetry test, an auto symmetry test, a stimulation test result screen, and a physical data input screen, all of which will be discussed hereinbelow.

Upon entry into the intra-operative procedures group screen 13, the computer system 1 requires initialization of a communications mode for the computer system 1 and the patient's transmitter 2. In the preferred embodiment, the user may select one of three modes: full control, read only, and demonstration. In full control mode, the computer system 1 and transmitter 2 may fully interact, wherein information and/or settings may be transferred from either source to the other for operation or storage. In read only mode, the transmitter 2 may upload stored information or settings from the transmitter's internal database to the computer system 1. Modifications or new information and settings, however, cannot be downloaded to the transmitter 2. In demonstration mode, no information can be transferred between computer system 1 and transmitter 2. Instead, demonstration mode, while appearing to operate in full communications mode, allows the computer system 1 to be demonstrated or used for training. Demonstration mode does provide, however, the ability to review patient information within the computer patient database.

Upon selection of either "full communications" or "read only" (provided the transmitter 2 is on and active), the computer system 1 establishes a communications link with the transmitter. If the computer system 1 cannot communicate with the transmitter 2, for whatever reason, the user is presented an appropriate notice reflecting such conditions and instructions posing alternative solution to secure a connection. Once such link is established, the computer system 1 queries the transmitter 2 to learn certain stored information, ensure the transmitter 2 is functional, and verify compatibility with the computer system 1.

Transmitter Results Summary mode 19 provides for an interchange of system and patient information between the computer system 1 and transmitter 2. Upon communication with a transmitter 2 for the first time, as is common during a first intra-operative procedure, the computer system 1 requests that information be uploaded from the internal transmitter database, such information may include the transmitter type and transmitter options (e.g., transmitter serial number, transmitter date of manufacture, etc.). This information is added directly to the patient's computer database file. Likewise, the Transmitter Results Summary mode 19 enables the transfer, or downloading, of patient and system information to the transmitter's internal database. The full use of this mode of operation will be more fully explored in the post-operative procedures group.

In the Manual Stimulation Test mode 14, the user may administer stimulation through the control of the computer system 1, rather than through the transmitter's controls. Specifically, through computer input mechanisms (e.g., keyboard and on-screen controls), the user chooses or defines new stimulation settings ("stimulation setting" meaning the values which define the polarity, if any, of each of the plurality of implanted electrodes and the delivered electric pulse's frequency, pulse width, phase and amplitude). If in "full control" communications mode, the selected or defined stimulation settings are downloaded to the transmitter for stimulation. Alternatively, when in "read only" mode, stimulation settings may be entered and/or modified; however, such information will not be transferred to the transmitter.

In a preferred embodiment, the Manual Stimulation Test mode 14 allows the requisite stimulation settings to be entered easily and without ambiguity. For example, in the preferred embodiment, the user could define the electrode combination through direct interaction with a graphical representation of each multi-electrode lead displayed on the computer's display screen. Through touching the representations with stylus 4, each electrode may be configured to assume a positive (anode), negative (cathode), or neutral polarity. If the patient's neuromodulation system supports differing electric pulse phases, the user could choose the electric pulse phase, i.e., monophasic or biphasic. Pulse width and frequency could also be adjusted through appropriate on-screen controls or making appropriate keyboard entries. The user initiates the stimulation by increasing the delivered amplitude of the stimulation setting above zero volts (default).

As stimulation amplitude is critical, the software preferably causes the amplitude to slowly increase at a rate of approximately 0.25 volts per second (notwithstanding, finer adjustments, such as 0.1 volt steps, could be programmed for each increment). The amplitude can be decreased in a similar fashion; however, the rate of decrease is preferably twice the rate of increase (for example, 0.5 volts per second). One skilled in the art will understand that the preferred rate of increase or decrease for amplitide control may differ for different modes or screens depending on whether the patient or a physician is the user. Control of the amplitude is achieved through either on-screen controls or keyboard entries. In the preferred embodiment, an emergency "off" control is provided to immediately terminate the delivery of a stimulation signal from the transmitter, i.e., the amplitude returns to its default setting, or zero 0 volts. If the user changes the electrode combination, the amplitude will return to its default setting. As pulse width and frequency are often used to better focus the delivered electrical pulse, these parameters can be adjusted without resetting the delivery amplitude. As one skilled in the art will appreciate, this embodiment is but one possible mode of operation. For example, amplitude may be determined by current rather than voltage. Variances of the electrical pulse by other characteristics, or by other dependent or independent parameters, shall be considered consistent with that disclosed herein.

Another intra-operative mode of operation includes the Manual Symmetry Testing mode 15. This test mode is used to verify lead symmetry and assess the region of influence of the applied stimulation for each tested stimulation setting. More specifically, during implantation of the lead(s), this mode 15 allows the physician the opportunity to monitor, control and optimize the applied electrical pulse's symmetry and region of influence. As should be noted, not all pain requires symmetrical, or bilateral, stimulation. Rather, bilateral stimulation is typically reserved for the management of bilateral pain, or that pain topography which encompasses both sides of the patient's body, including the midline.

Operatively, the user programs a first stimulation setting in a manner consistent with the procedure described earlier for the Manual Stimulation Test mode 14. The user then increases the stimulation amplitude until the patient just begins to feel stimulation ("perception threshold"). The patient is asked to indicate whether the stimulation is felt on the left side, the right side or both sides of the body, wherein perceived stimulation of either the left or right sides is termed "unilateral" stimulation and the simultaneous stimulation of both sides is referred to as "bilateral" stimulation. If the patient experiences only unilateral stimulation, the user continues to increase the amplitude until the patient indicates either bilateral stimulation ("bilateral threshold") or minor, involuntary muscle contractions are observed. As a means of evaluating the symmetry of the stimulation, the computer system compares the ratio of the bilateral threshold to the perception threshold, such ratio value being analyzed relative to the perception amplitude value. For example, symmetry could be defined to occur if B/P<1.1. Continuing, upon achieving and indicating bilateral stimulation, the user increases the amplitude until the patient experiences minor, involuntary muscle contractions ("motor threshold"). From this information, the software of the present invention determines a "beginning stimulation amplitude." For example, in the preferred embodiment, the beginning stimulation amplitude equals the $60^{th}$-percentile level (60 percent of the difference between the motor and the perception thresholds, added to the perception threshold).

Figure 7:
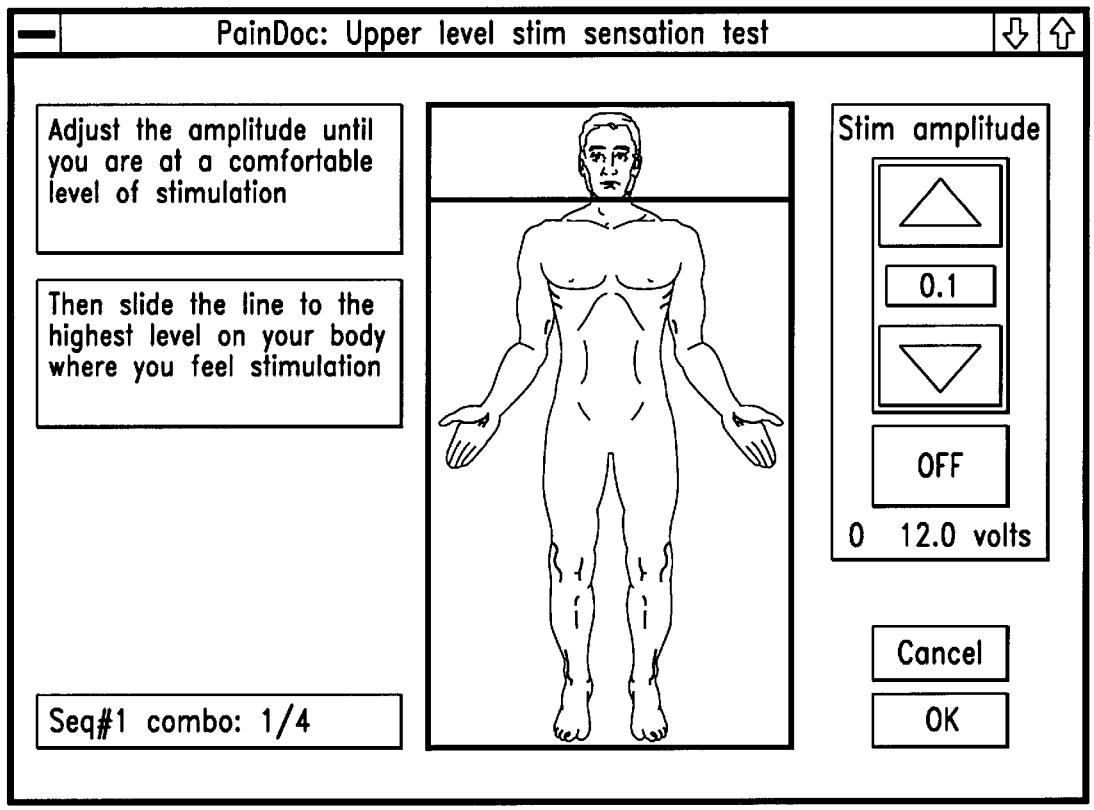
FIG. 7 is a depiction of the upper limit region of stimulation influence display of the system, showing a human representation and an upper limit stimulation indicator.
Figure 8:
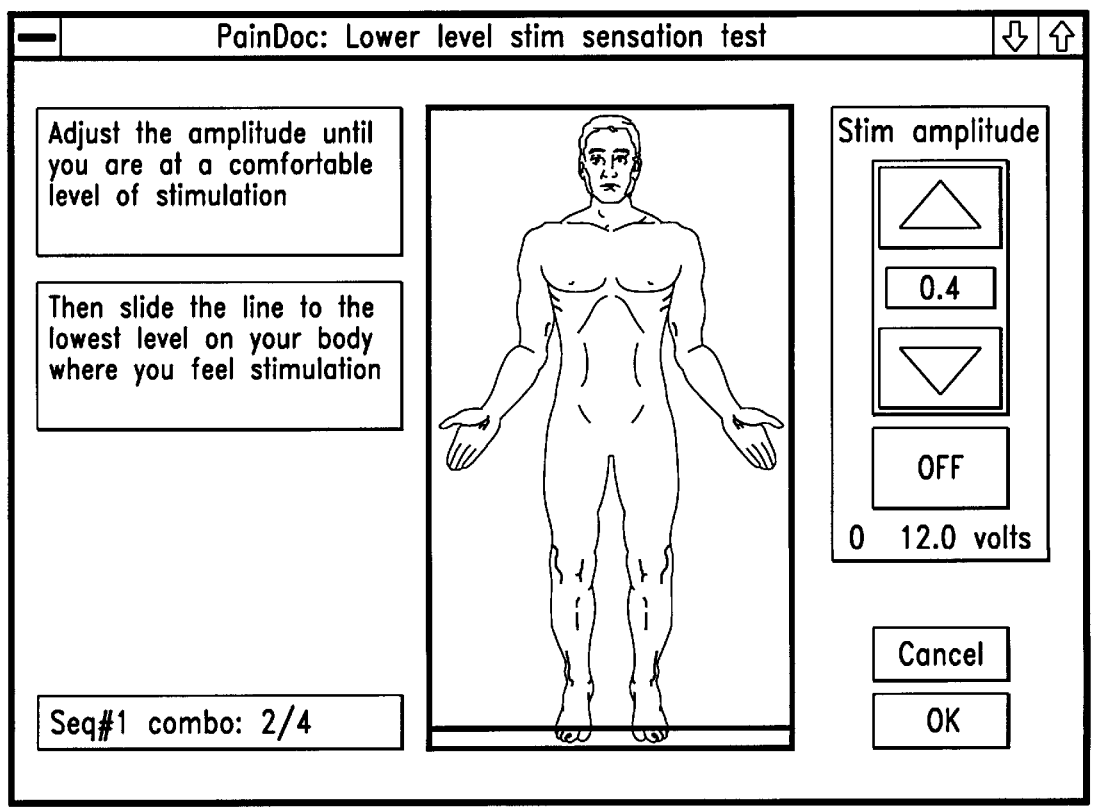
FIG. 8 is a depiction of the lower limit region of stimulation influence display of the system, showing a human representation and an lower limit stimulation indicator.

Stimulating the patient at this beginning stimulation amplitude, the user is prompted to define the region of stimulation influence. The method of the preferred embodiment requires the user to define this region by positioning stimulation limit indicators at the upper and lower most level of perceived stimulation (see FIGS. 7 and 8, respectively). Upon definition of this region, the amplitude is reset to zero and the computer system assesses whether the patient's pain is contained within upper and lower, patient-defined boundaries.

If all pain is located within the defined region, the system may be programmed to display such information. If some portion of the pain extends outside the region, the system can be also programmed to display a message indicating this condition. In this later scenario, the computer system 1 can be further programmed to suggest specific alternatives to assist in broadening the region of stimulation influence. As an example of such alternatives, the computer system 1 may suggest varying the stimulation setting, adding additional stimulation settings for advanced stimulation procedures and/or implanting additional multi-electrode leads (the latter example being contingent upon the patient's neuromodulation system being capable of receiving or supporting additional leads).

Upon concluding the computer system's region of influence evaluation, the user is permitted to program another stimulation setting. If so elected, the user returns to the beginning of the Manual Symmetry Test mode 15 to repeat the above steps. Alternatively, the user may elect to review a summary of the intra-operative test results by advancing to the Stimulation Test Results screen 18, which such screen will be discussed further below. If the user elects none of the above options, the user returns to the intra-operative procedures group screen 13.

Functionally similar to Manual Symmetry Mode 15, the preferred embodiment of the present invention also includes an Auto-Symmetry Test mode 16. Differing from its manual counterpart, Auto-Symmetry Test mode 16 permits the assessment of the symmetry and region of stimulation influence of a number of predefined electrode combinations (determined as a function of the patient's neuromodulation system) and/or computer-suggested electrode combinations. The computer-suggested combinations are a function of, at least, the patient's physical condition, the patient's unique pain pattern and the patient's neuromodulation system. During the implantation of the leads, the physician can observe and optimize the stimulation effect through the adjustment of the stimulation pulse frequency, pulse width, phase and amplitude. The physician may accept the suggestions or terminate this mode of operation at any time.

In addition to offering predefined or computer-suggested electrode combinations, the Auto-Symmetry Test mode 16 assists the physician in assessing the placement of the multi-electrode lead(s). Through the evaluation of the perception, bilateral and motor amplitudes (such being entered for each electrode combination in a manner similar to that for the Manual Symmetry Test mode 15), the computer system 1 can be programmed to prompt and direct the physician to reposition the lead(s) to achieve better stimulation. Examples of such prompts and directives, and the basis for such, may include:

| Initial Perception | Bilateral/Perception Amplitude Ratio (x) | Prompt/Directive |
|---|---|---|
| Left | x > 1.3 | Lead too close to nerve root. Reposition lead to right. |
| Right | x > 1.3 | Lead too close to nerve root. Reposition lead to left. |

-continued

| Initial Perception | Bilateral/Perception Amplitude Ratio (x) | Prompt/Directive |
|---|---|---|
| Left | 1.15 < x < 1.3 | Move lead closer to the midline. Reposition lead to the right. |
| Right | 1.15 < x < 1.3 | Move lead closer to the midline. Reposition lead to the left. |

Once the multi-electrode lead(s) is positioned, without regard to the physicians' use of mode 15 or mode 16, the physician may enter the physical position of the lead(s) via the Physical Data Input screen 17. In particular, the physician inputs the vertical and horizontal locations of the multi-electrode lead(s) from actual measurements taken from an x-ray of the patient's spine. This information can be stored not only in the patient's computer database file but also the transmitter's database. The value of this information is readily apparent when one appreciates that percutaneous multi-electrode leads have the ability to migrate over time. Often times, changes in stimulation location or stimulation efficacy may be attributable to lead migration, therefore, the present invention further empowers the patient's physician to quickly diagnose and, if possible, remedy stimulation based on lead movement.

A summary of the intra-operative activities may be reviewed within the Stimulation Test Result screen 18. The screen can convey at least the following information for each stimulation setting tested: the date of stimulation; the stimulation setting (electrode combination, pulse frequency, pulse width, phase); the perception, bilateral and motor thresholds; and various assessment ratios of these thresholds.

The computer system includes a communication message processor module 20 and communication driver 21 to facilitate communications to the transmitter.

Post-Operative Procedures Group

Figure 4:
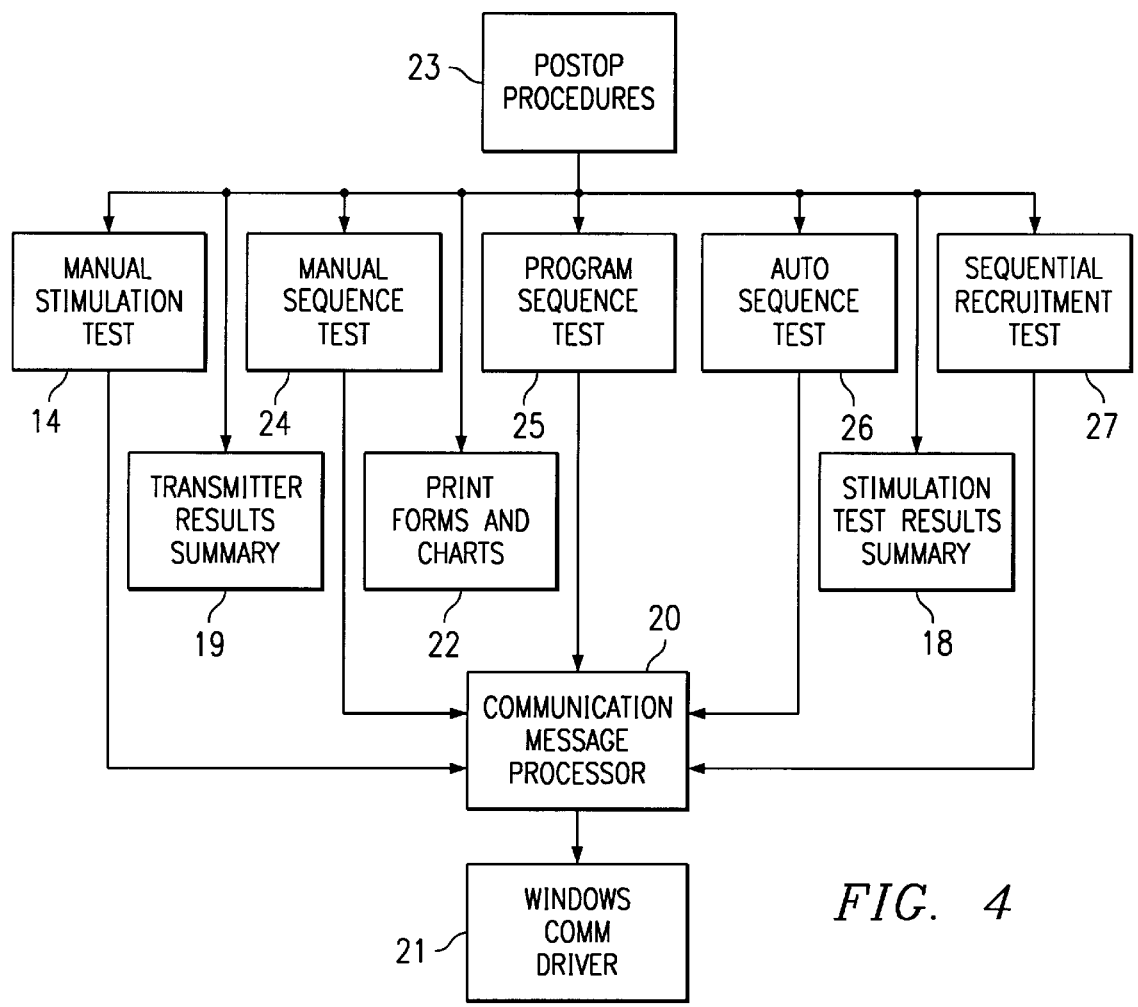
FIG. 4 is a flow diagram depicting the post-operation procedures that can be performed using the system of the invention.

Referring to FIG. 4, the system also operates in a post-operative mode 23. The post-operative procedures group provides a vehicle for the continued support and optimization of a patient's post-implantation stimulation. As the objectives for intra-operative and post-operative operations are largely similar, the preferred embodiment of the present invention includes screens and modes which do not substantively differ between the two procedures groups. Although the post-operative procedures group includes additional functions, this group may include a communications selection mode (for establishing a communications link between the computer system and the patient's transmitters), Manual Stimulation Test mode 14, Stimulation Test Results mode 18 and Transmitter Results Summary mode 19, which appear and function just as the modes were disclosed and defined hereinabove for the intra-operative procedures group.

Looking again at the Transmitter Results Summary mode 19, this mode of operation provides a means of comparing the patient's neuromodulation system against the information within the patient's computer database file. The transmitter database, and the information in which it maintains, serves various purposes, such including: (i) assurance that a patient's system information is consistent with the patient's computer database file; and (ii) provision of critical treatment and system data to a physician who is not the patient's normal physician and may not have a full appreciation for the patient or the patient's system. Addressing the former, inconsistencies may serve as a identification system (for example, to identify loaner transmitter equipment) or as a basic warning mechanism (for example, to indicate at least a memory failure within the transmitter or that the patient possesses a system other than their own). Depending upon the nature of the inconsistency, the Transmitter Results Summary mode 19 further includes an editing feature in which differing information may be reconciled.

Referencing those differing features of the post-operative procedures group, the Manual Sequence Test mode 25 requires a new stimulation setting to be defined in a manner consistent with the Manual Stimulation Test mode 14 described hereinabove. After setting the electrical pulse frequency, pulse width, and phase, the user enters an electrode combination. Electrical stimulation is administered to the patient in accordance with the defined stimulation setting. For each electrode combination, the user determines and records the perception, bilateral and motor thresholds, also in a manner consistent with mode 14. In the preferred embodiment, the patient draws a stimulation map based upon the perceived stimulation effect at some known stimulation amplitude (for example, 60 percent of the difference between the motor and the perception amplitudes, added to the perception amplitude). The computer system evaluates and compares the stimulation map to the patient's pain map.

In the Sequential Recruitment Test mode 27, a single combination of parameters or a programmed sequence of combinations, can be tested relatively quickly. This method also produces more quantitative results, while consuming less time than the qualitative methods. As with most other tests, the patient is requested to determine the electrical intensity at which stimulation is first perceived. As before, he also finds the threshold for bilateral spread of stimulation. The patient's pain map drawing is then used to extract several important targets ("targets" means specific body regions which are associated with known types of pain). For each of these few important targets, the patient is required to produce a threshold value for the "recruitment" or coverage of the particular targets with percieved stimulation. These targets are clinically relevant and they are derived from stimulating the spinal cord, and interpreted through the use of recognition algorithms, stored in the computer. For instance, for the common problem of pain of low back and legs, thresholds would be obtained for these targets: each anterior thigh; the heel of the the foot on the more symptomatic leg; the more-symptomatic buttock; and the low back. Sometimes, the threshold for recruiting another target contributes useful information: e.g. the groin, the low abdomen, or the great toe. As another example, when the testicle is also in pain, the threshold for its recruitment would be recorded, independent of other targets. The final threshold is identical to that obtained by the other tests: the motor threshold. Without this amplitude value, the other threshold cannot be well normalized.

The efficacy of the stimulation setting, in addition to being measured by the Sequential Recruitment test mode 27, may be measured by the percentage of overlap of the stimulation map and pain map, with smaller weighting given to the percentage of "extraneous stimulation" (that electrical stimulation delivered to a dermatome, partial dermatome or multiple dermatomes otherwise unaffected by pain). An optimum stimulation setting would possess the attributes of: 100 percent overlap; first perceived paresthesia located at the most painful target; side effects located at a non-noxious location; and, 0 percentage of extraneous stimulation.

In the Program Sequence Test mode 25, either a physician may program a sequence, or series, of stimulation settings or the computer system generates a sequence of stimulation settings based upon, at least, the patient's physical conditions, the patient's unique pain pattern and the patient's neuromodulation system. Without regard to the origination of the sequence, the computer guides the patient through the assessment procedure, minimizing the need for physician supervision. As the sequence is run, the patient is requested to respond and enter data which will result in a determination of related perception, bilateral, other painful target, and motor thresholds as well as a stimulation map. The patient, under physician supervision, may adjust the characteristics (e.g., frequency, pulse width and phase) of the setting during the response period.

The computer system preferably compares the stimulation map to the patient's pain map for percentage overlap, for ease of stimulating the most painful target(s) (thresholds measured in mode 27), and percent of extraneous stimulation. As the sequence of settings are evaluated and completed, such results are stored for later review in the Stimulation Test Results screen 18. The Simulation Test Results screen 18 presents each stimulation setting and its results in a manner that facilitates unambiguous comparison between the settings. The presentation of such information further assists the physician in the decision to accept those stimulation settings tested or to continue the evaluation procedure in a manner which involves a process of elimination of relatively less useful stimulating parameters.

Figure 9A:
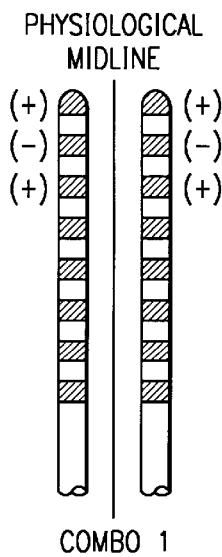
FIG. 9 illustrates one embodiment of the multi-electrode lead evaluation combinations as defined and assessed within the post-operative procedures group.
Figure 9B:
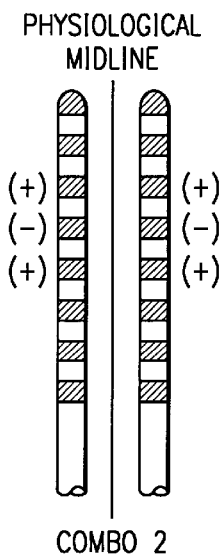
Figure 9C:
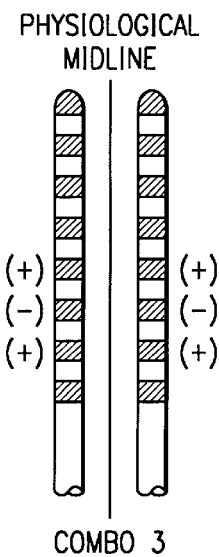

In the Automatic Sequence Test mode 26 the computer system undertakes a systematic, iterative routine to determine and optimize the patient's stimulation settings. In the preferred embodiment, the computer system proposes a number of stimulation settings based upon the movement of a basic electrode combination along the electrodes of a multi-electrode lead(s). For example, mode 26 can be illustrated using two eight electrode leads. The leads should be longitudinally aligned and positioned in parallel, an equal distance on either side of the physiological midline. The computer may begin with an electrode row combination in which the distal-most electrode row is defined as an anode (+), the next lower electrode a cathode (−) and the next lower electrode as an anode, the remaining five electrodes assume a neutral polarity. Following the definition of the various characteristics of the electrical pulse (e.g., frequency, pulse width, phase), the amplitude is increased to the point of perception, bilateral stimulation, recruitment of relevant painful targets, and the occurrence of minor, involuntary muscle contractions (each being indicated and recorded in a manner consistent with earlier discussed screens and modes). This procedure is repeated, for example, two additional times with the basic electrode row configuration merely "changing position" with respect to the multi-electrode leads. Using the basic electrode row configuration example of above, the second setting ("COMB02") would find the upper most anode of the basic electrode row configuration at the third electrode row from the end of the leads. Likewise, the third setting ("COMB03") would find the upper most anode at the fifth electrode from the end of the leads. FIG. 9 illustrates each of the above test combinations.

In the event symmetry cannot be obtained for one of the proposed stimulation settings, the computer system will modify and retest the setting in accordance with the following rules:

| Step | Condition | Action |
|------|-----------|--------|
| 1 | Asymmetrical, B/P* > 1.5 | Delete anodes on stronger side. |
| 2 | Continued asymmetrical | Return anodes on stronger side, delete cathode from strong side, delete anodes form weak side. |
| 3 | Continued asymmetrical | Delete anodes on strong side, restore anode(s) to weak side. |
| 4 | Continued asymmetrical | Delete upper-most anode. |
| 5 | Continued asymmetrical, B/P < 1.5 | Take best combination with lowest B/P |
| 6 | B/P > 1.5 | Abandon combination |

*- Ratio of bilateral threshold to perception threshold.

If the combination is abandoned, the computer system will provide an alternative electrode combination ("COMBOn") for re-evaluation.

As the stimulation effect of each combination will ultimately be evaluated and compared (against one another as well as other stimulation settings), it is important that the intensity, or the perceived intensity, of the stimulation be subjectively comparable. Otherwise, data may be gathered, and consequently relied uponn during optimization, which is misleading and does not effectively contribute to addressing a particularized pain pattern. Interestingly, a patient can confuse the effects of extraneous stimulation, produced by excessive amplitudes, with effective, localized stimulation. In an attempt to minimize such occurrence, the computer system 1 enters a normalization mode, whereby the patient undertakes to normalize the perceived intensity of the differing stimulation settings.

As first introduced in the Manual Symmetry Testing mode 15 of the intra-operative procedures group, the computer system 1 computes the $60^{th}$-percentile stimulation amplitude for each stimulation setting (e.g., COMBO1, COMBO2, COMBO3). The patient is asked to compare the "feeling," or intensity, of two combinations (e.g., COMBO1 and COMBO2), such combinations being executed sequentially. The patient adjusts the amplitude of the perceived "weaker" combination upward. Wherein the "weaker" combination approaches the motor threshold and an equalization has not been achieved, the amplitude of the "stronger" combination is stepped downward. Once these combinations are normalized, this procedure is repeated with one combination of the prior procedure and a remaining, un-normalized combination (e.g., COMBO2 and COMBO3). Upon normalization of each combination, the computer system 1 automatically executes each combination for a brief duration. If the combinations are believed equivalent in subjective intensity, the computer system undertakes a similar procedure for normalization of the combinations' motor thresholds. If not, the patient is required to undergo the normalization procedure again.

Following normalization, the patient is asked to assess the stimulation effect of each combination against the patient's overall and worst pain maps. If each of the combinations cover both the overall and worst pain, the computer system will reduce the amplitude by a first fixed amount (for example, 50%) and retest the combinations' coverage. If coverage is maintained, the computer system will continue to reduce the amplitude by a second fixed amount (for example, 10%), each reduction being evaluated for coverage, until only one combination possesses the greatest overall pain coverage for the least amount of amplitude (expressed as a percentage of P).

In the event no combination entirely covers the overall and/or worst pain maps, the computer system can be programmed to increment the amplitude of one or more of the electrode combinations in an attempt to attain better pain/stimulation overlap. If total coverage cannot be achieved, the patient should draw a stimulation map for the purpose of determining a relative "score" of each combination. This score will enable a later qualitative evaluation of all tested combinations.

If the patient desires to evaluate additional combinations, the computer system can present another electrode combination group. Although this and subsequent groups can utilize the same basic electrode combination, the electrode combinations will be "positioned" at differing levels along the multi-electrode lead. Ultimately, the chosen combinations of each group will be combined for a trial assessment and determination of the most effective stimulation settings.

Notwithstanding the means undertaken to create one or more stimulation settings through the post-operative procedures group, the intention is to identify and download at least one stimulation setting which addresses and adequately masks the patient's pain. If the transmitter 2 is of that type described in co-pending patent application, Ser. No. 00/000,000, filed Apr. 0, 1996, which is incorporated herein by reference, a plurality (of at least three) stimulation settings may be downloaded to transmitter 2 to provide continuous or intermittent management of diffuse, multi-focal pain. Furthermore, a plurality of stimulation settings can be downloaded so the patient may compare their relative efficacy across longer durations.

The computer system 1 of the present invention may include an internal or external modem device (not shown) for communication with other computers of this invention or a centralized resource computer. Through such means, the computer system of the present invention may, from a remote location, receive software maintenance as well as upload/download patient and stimulation setting information. As the centralized resource computer comes to realize more and more patient and stimulation setting information, the present invention becomes increasingly valuable. In part, the present invention, having a greater population of information in which to search and evaluate, can improve its assessments and suggestions with regard to any one particularized pain pattern.

The above description relates to the preferred mode of our invention. Variations and additional features and functions within the skill of the art, including advances in computers and input devices are intended to be covered.

We claim:

1. A method for anatomically positioning electrodes that are part of a neurological stimulator, the method comprising the steps of:

initially positioning the electrodes in the body of a patient;

selecting a stimulation program that has a variable parameter;

applying stimulation in accordance with the stimulation program;

intraoperatively adjusting the variable parameter and recording, by patient response, the variable parameter at which stimulation is perceived;

intraoperatively adjusting the variable parameter and recording, by patient response, the variable parameter at which stimulation is perceived bilaterally;

intraoperatively adjusting the variable parameter and recording, by patient response, the variable parameter at which motor response occurs;

intraoperatively administering electrical stimulation having a pulse characteristic determined as a fuction of at least one of the previously recorded variable parameters; and if necessary, physically repositioning the electrodes for more effective coverage of an area afflicted by pain based upon at least one of the previously recorded variable parameters.

2. The method of claim 1, further including the step of recording, by patient response, a highest and a lowest points on the patient's body where stimulation is perceived as a consequence of administering electrical stimulation having the pulse characteristic.

3. The method of claim 1, further including the step of determining symmetry of stimulation through evaluation of at least one of the previously recorded variable parameters as recorded at perception bilateral perception, and at motor response.

4. The method of claim 1, wherein the variable parameter is stimulation amplitude.

5. The method of claim 1, further comprising the step of instructing a direction in which to physically move the electrodes based upon a ratio of the variable parameters as recorded for bilateral perception and initial perception.

6. A system for selecting effective electrode stimulation patterns in a computer controlled neuromodulation system comprising:
    means for storing and applying an initial electrical stimulation pattern defined by an initial electrode configuration and at least one variable parameter;
    means fro recording at least an initial representation of patient-corresponding regions afflicted by pain as well as a representation of an effect of the initial electrical stimulation pattern which causes at least a perceptible response;
    means for comparing the representation of an effect of the initial electrical stimulation pattern to the representation of patient-corresponding regions afflicted by pain and generating a result corresponding thereto; and
    means for generating at least a new suggested electrode configuration based upon a level of sufficiency of the result.

7. A method for anatomically positioning electrodes that are part of a neurological stimulator, the method comprising the step of:
    initially positioning the electrodes in a patient's body;
    intraoperatively applying a predetermined stimulation program that has a variable amplitude;
    intraoperatively adjusting the amplitude and recording, by patient response, the amplitude at which stimulation is perceived;
    intraoperatively adjusting the amplitude and recording, by patient response, the amplitude at an occurrence of an event;
    recording, by patient response, an indication as to whether the stimulation was to the left or right of the patient's body; and
    when the event is that a motor response occurs before a bilsteral perception, displaying suggested reositioning instructions for the electrode based upon a ratio of the recorded amplitudes and the indication as to whether the stimulation was to the left or right of the patient's body.

8. The method of claim 7, wherein when the event is that motor response occurs before bilateral perception, further comprising the step of recording, by patient response, which side of the patient's body stimulation was perceived.

9. A method for determining at least one effective electrode stimlation pattern in a computer controlled neuromodulation system having at least one multi-electrode lead implanted within a patient's body, the method comprising the steps of:
    (a) administering electrical stimulation for a predetermined electrode configuration at a first position relative to the at least one multi-electrode lead, wherein the electrode configuration causes a number of electrodes to be positive and a number of electrodes to be negative, the positive and negative electrodes having a prescribed polarity arrangement;
    (b) serially administering electrical stimulation for the electrode configuration at a second position relative to the at least one multi-electrode lead, wherein at least one of the electrodes of the at least one multi-electrode lead differs in polarity from step (a) to step (b) but the prescribed polarity arrangement remains unchanged;
    (c) recording, by patient response, at least one variable parameter of the electrical stimulation in which the electrical stimulation causes at least one perceptible response, such recording occurring for each position of the electrode configuration;
    (d) comparing a perceived effect of the electrical stimulation at each position; and
    (e) selecting at least one position from such comparison.

10. The method of claim 9, further including the step of normalizing patient-perceived electrical stimulation intensity at each position of the electrode configuration to facilitate the comparison of step (d), wherein the step of normalizing is performed prior to step (d).

11. The method of claim 9, in steps (a) and (b) when the administered stimulation is asymmetrical but symmetrical stimulation is desired, further including the step of automatically reconfiguring the electrode configuration based upon the patient response to achieve stimulation symmetry at the position relative to the at least one multi-electrode lead in which asymmetrical stimulation was administered.

12. The method of claim 11, wherein if symmetrical stimulation cannot be achieved, further comprising the steps of: abandoning the electrode configuration; generating a new electrode configuration; and repeating steps (a) and (b) using the new electrode configuration.

13. The method of claim 9, in steps (a) and (b) when the administered stimulation is asymmetrical but symmetrical stimulation is desired, further including the step of automatically reconfiguring the electrode configuration and varying at least one variable parameter based upon the patient response to achieve stimulation symmetry at the position relative to the at least one multi-electrode lead in which asymmetrical stimulation was administered.

14. The method of claim 13, wherein if symmetrical stimulation cannot be achieved, further comprising the steps of: abandoning the electrode configuration; generating a new electrode configuration; and repeating steps (a) and (b) using the new electrode configuration.

15. A system for analyzing patient responses to aid in positioning electrodes of a neuromodulation system, the system comprising:
    a neuromodulation system, having an implanted receiving device and at least one lead having a plurality of electrodes which is coupled to the receiving device, to administer stimulation to selected tissue of a patient, wherein the receiving device generates electrical energy for delivery to the at least one lead which is coupled thereto;
    a general purpose computer, the computer being capable of communicating with the receiving device to define the electrical energy generated by the receiving device;

sofware for recording patient responses to applied stimulation, the stimulation being administered in accordance with a stimulation setting having a plurality of variable parameters; and software for displaying suggestions for at least one alternative stimulation setting as a function of the recorded patient responses.

16. The system of claim 15, wherein the suggestions include instructions for physically repositioning of the electrodes.

17. The system of claim 15, wherein the suggestions include a new stimulation setting.

18. A method for determining a stimulation setting for a neurological stimulator having at least one multi-electrode lead to provide a desired stimulation effect in a human body, where the stimulation effect corresponds to the stimulation setting, the method comprising the steps of:

initially positioning the at least one multi-electrode lead in the body of a patient;

selecting a stimulation setting having a variable parameter;

applying stimulation in accordance with the stimulation setting;

intraoperatively adjusting the variable parameter and recording, by patient response, the variable parameter where a desired stimulation perception occurs;

intraoperatively administering electrical stimulation having a pulse characteristic determined as a function of the desired variable parameter previously recorded; and determining a new stimulation setting with a computing device based upon the previously recorded variable parameter.

19. The method of claim 18, wherein the desired stimulation perception includes at least an initial perception of stimulation.

20. The method of claim 18, wherein the desired stimulation perception includes at least a bilateral perception of stimulation.

21. The method of claim 18, wherein the desired stimulation perception includes at least a motor response.

22. A method for anatomically positioning electrodes that are part of a neurological stimulator, method comprising the steps of:

initially positioning the electrodes in the body of a patient;

selecting a stimulation setting having a variable parameter;

applying stimulation in accordance with the stimulation setting;

intraoperatively adjusting the variable parameter and recording, by patient response, the variable parameter where a desired stimulation perception occurs;

intraoperatively administering electrical stimulation having a pulse characteristic determined as a function of the desired variable parameter previously recorded; and if necessary, physically repositioning the electrodes for more effective coverage of the area afflicted by pain based upon the previously recorded variable parameter.

23. The method of claim 22, wherein the desired stimulation perception includes at least an initial perception of stimulation.

24. The method of claim 22, wherein the desired stimulation perception includes at least a bilateral perception of stimulation.

25. The method of claim 22, wherein the desired stimulation perception includes at least a motor response.

26. A system for selecting effective electrode stimulation patterns in a computer controlled neuromodulation system, the system comprising:

means for storing and applying an initial electrical stimulation pattern defined by an initial electrode configuration and at least one variable parameter of the initial electrical stimulation pattern;

means for recording at least an initial representation of patient-corresponding regions afflicted by pain and a representation of an effect of the initial electrical stimulation pattern which causes at least a perceptible response;

means for comparing the representation of an effect of the initial electrical stimulation pattern to the representation of patient-corresponding regions afflicted by pain and generating a result corresponding thereto; and means for generating at least one new variable parameter for the initial elecrical stimulation pattern based upon a level of sufficiency of the result.

* * * * *

UNITED STATES PATENT AND TRADEMARK OFFICE
CERTIFICATE OF CORRECTION

PATENT NO.   : 5,938,690  
DATED        : August 17, 1999  
INVENTOR(S)  : Jay Law, William Borkan, Lance Ehren, and George Van Campen It is certified that error appears in the above-identified patent and that said Letters Patent is hereby corrected as shown below:

Title page,
Item [75], Inventors, delete "Jay Law, Denver, Colo.; William Borkan, North Miami Beach, Fla.; Lance Ehren, Dallas, Tex.; George Van Campen, Fort Lauderdale, Fla.", and insert "Jay Law, Denver, Colo.; William Borkan, North Miami Beach, Fla.; Lance Ehren, Dallas, Tex.; George Van Campen, Fort Lauderdale, Fla.; Richard B. North, Baltimore, Maryland".

Signed and Sealed this

Twenty-fifth Day of December, 2001

*Attest:*

*Attesting Officer*

JAMES E. ROGAN
*Director of the United States Patent and Trademark Office*